United States Patent [19]

Thorud et al.

[11] Patent Number: 5,546,958
[45] Date of Patent: Aug. 20, 1996

[54] GUIDEWIRE EXTENSION SYSTEM WITH TACTILE CONNECTION INDICATION

[75] Inventors: Michael S. Thorud, Bloomington; Robert L. Assell, Mendota Heights, both of Minn.

[73] Assignee: Lake Region Manufacturing Company, Inc., Chaska, Minn.

[21] Appl. No.: 220,902

[22] Filed: Mar. 31, 1994

[51] Int. Cl.⁶ ........................................................ A01B 5/00
[52] U.S. Cl. ............................................ 128/772; 128/657
[58] Field of Search ................................... 128/772, 657; 604/95, 104, 280, 281, 282, 283

[56] References Cited

U.S. PATENT DOCUMENTS

| | | | |
|---|---|---|---|
| 4,790,825 | 12/1988 | Bernstein et al. | 128/772 X |
| 5,109,867 | 5/1992 | Twyford, Jr. | 128/772 |
| 5,117,838 | 6/1992 | Palmer et al. | 128/772 |
| 5,139,032 | 8/1992 | Jahrmarkt et al. | 128/772 |
| 5,188,621 | 2/1993 | Samson | 128/772 X |
| 5,197,486 | 3/1993 | Frassica | 128/772 |
| 5,247,942 | 9/1993 | Prather et al. | 128/772 |

*Primary Examiner*—Sam Rimell
*Attorney, Agent, or Firm*—Grady J. Frenchick; Stroud, Stroud, Willink, Thompson & Howard

[57] ABSTRACT

A guidewire extension system including a guidewire and an extension wire is disclosed. The system includes female and male connector segments located on the proximal end of the guidewire or the distal end of the extension wire. The hollow female connector segment, in one embodiment, includes a radial lip which intersects with lateral slots. The male connector segment includes an external groove. When the male connector is inserted into the female connector segment, the slots are expanded and the lip snaps into the groove providing a tactile indication that connection is completed.

No restriction or frictional fit is created. The guidewire and extension wire are freely rotatable with respect to each other and can be multiply connected and disconnected. Methods of catheter exchange with tactile indication of guidewire extension wire connection are disclosed.

13 Claims, 14 Drawing Sheets

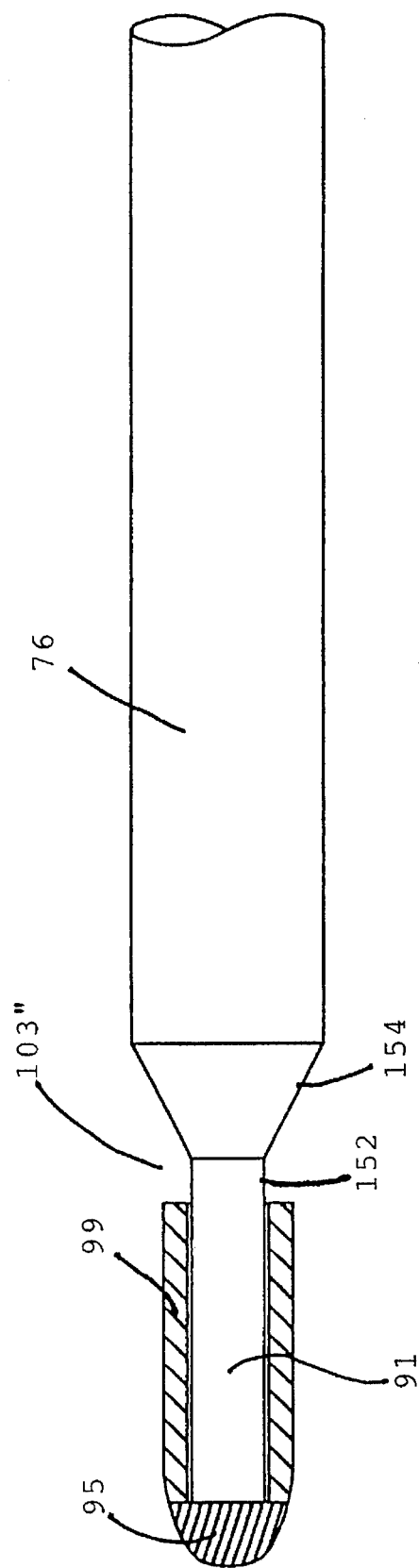

GUIDEWIRE EXTENSION SYSTEM WITH TACTILE CONNECTION INDICATION

FIELD OF THE INVENTION

The present invention relates in general to the field of guidewires. Guidewires are used to position catheters in exploratory procedures, diagnosis, and treatment of various medical conditions. More particularly, this invention relates to a guidewire extension system for connecting or coupling a guidewire, primary or initial wire to an extension or secondary wire during a medical procedure.

BACKGROUND OF THE INVENTION

Guidewires are used in various medical procedures to position medical devices at desired locations within a patient's vascular system. Guidewires, which are steerable, are inserted and maneuvered through the patient's vasculature to a previously chosen location. Once in place, the guidewire provides the means to place a non-steerable device, such as an over the wire catheter, at the chosen body site. For example, a catheter is slid over the guidewire until the catheter, or some working portion thereof, is positioned within the vasculature at the desired location. Generally speaking, guidewires of a standard length are longer than the non-steerable devices with which they are used to permit independent movement of the device and the wire.

Angioplasty is one interventional procedure where a guidewire is often used. In angioplasty a dilatation catheter having an inflatable balloon structure is used to compress occlusive or blockage material against the sides of a vessel, thereby permitting (ideally) circulation to be reestablished. In preparatory procedures, the site of a vascular restriction, occlusion or stenosis is identified. In the usual procedure, the guidewire is inserted into the patient's femoral artery and maneuvered or steered to the location of the restriction. Maneuvering of the guidewire is facilitated by a video X-ray device which allows the physician to observe the movement of the guidewire's distal tip. The guidewire distal tip generally comprises a radiopaque metal to enhance X-ray viewing. A dilatation catheter then is inserted over the guidewire so that its working segment is located adjacent the restriction. Generally this means that the catheter balloon is positioned adjacent the vascular restriction or blockage.

During a simple angioplasty procedure, the dilatation catheter balloon is inflated to open the restriction, and then is removed along with the guidewire. However, complications sometimes arise which prevent the physician from completing this simple procedure. Occasionally the balloon catheter malfunctions. Sometimes a larger (or smaller) balloon is required further to dilate the vascular restriction, or another device or other type of catheter is needed to remove vascular material. For whatever the reason, the guidewire extension system of this invention is used when the catheter, or other such device, has to be removed and replaced with another device or catheter.

In the usual procedure to exchange catheters, the guidewire is removed from the patient, leaving the catheter in the vascular system. An exchange wire is inserted through the catheter and the catheter removed, leaving the exchange wire in place. The new catheter is inserted over the exchange wire and the exchange wire removed and replaced with the guidewire.

It is desirable to keep the guidewire in the patient's vasculature for various reasons. One reason is that the initial placement of the guidewire requires extensive, time consuming, manipulation. Removal and repositioning of the guidewire would be equally time consuming, possibly requiring a patient to be exposed to additional drugs, radiation, and, in general, infliction of additional trauma to the patient. It is also of importance that once the guidewire has been steered to a position across a lesion, that the crossed lesion position not be lost by removal of the guidewire. Guidewires removed from a crossed lesion may induce spontaneous vascular restriction or closure making repositioning of the guidewire difficult if not precluded.

In those cases where catheter exchange is desired, the physician would simply prefer to remove the catheter over the guidewire, leaving the guidewire positioned in the patient. However, to permit catheter exchange, a guidewire over which a catheter is to be exchanged must be sufficiently long to allow the physician to grip a portion of the wire as the catheter is being withdrawn over the guidewire. This requires the guidewire to be long enough to provide an external portion longer than the catheter in addition to the guidewire portion remaining in the patient.

Unfortunately, a guidewire of sufficient length to provide suitably long external and internal portions has inferior handling characteristics, thereby making more difficult the steering and maneuvering manipulations needed for guidewire placement. The added length also imposes itself on the usually cramped vascular suite thereby causing distractions from other support activities. It is for these reasons that guidewires are usually only slightly longer than balloon catheters, e.g. 20–50 centimeters longer, and that a much longer exchange wire is used only with exchange procedures.

Illustrating the above, a dilatation catheter has a shaft length in the range of about 120 cm to about 150 cm, a suitable guidewire for such a catheter would have a length in the range of about 150 cm to about 180 cm and an exchange wire would have a length in the range of about 260 cm to about 300 cm. As can be imagined from the above, utilization of an exchange wire in an exchange wire procedure is complicated and time consuming. This invention simplifies catheter exchange and eliminates the need to use an exchange wire.

A recent development involves coupling or connecting a second length of wire, sometimes called an extension wire or secondary wire, to the exposed, proximal end of a positioned guidewire. The secondary wire length should be sufficient to allow the catheter to be withdrawn while leaving the primary or lesion crossing guidewire in the patient. Various approaches have been suggested for effecting the attachment of an extension wire to a guidewire.

In one approach, such as that described in U.S. Pat. No. 4,922,923 to Gambale et al., a guide wire and an extension are joined together by crimping. A special crimping tool is disclosed in the Gambale et al., '923 patent. A drawback of this approach is that once the wires have been crimped, the connection therebetween is substantially permanent, and the extension wire cannot be detached from the guidewire except by severing it, e.g., by cutting.

Instead of crimping the guidewire to the extension wire, attempts have been made to engage the extension wire to the guidewire frictionally. Such attempts are described, for example, in U.S. Pat. No. 5,113,872 to Jahrmarkt et al., and related U.S. Pat. No. 5,117,838 to Palmer et al. These two patents disclose a guidewire extension system in which the distal end of the extension wire comprises a small diameter tube in which there is disposed a small diameter, open pitch, flat wire coiled spring. The proximal end of the guidewire has a reduced diameter portion which is inserted into the tube assembly to complete the connection. The reduced diameter proximal end of the guidewire is slightly larger than the internal diameter of the coiled spring of the extension wire, thereby creating a frictional engagement when one is inserted into the other. Palmer et al. disclose the utilization of a swivel joint for minimizing twisting of the extension guidewire when connecting or disconnecting it from the extension wire. A device as described in these two patents would be very difficult to manufacture reliably and apparently requires an alignment tool to ease insertion.

U.S. Pat. No. 4,875,489 to Messner et al., discloses an extendable guidewire in which concentric tubular segments are secured to one or the other of the sections to be connected. The inner tubular segment has a longitudinal slot therein which permits it to expand when a cooperating male portion is inserted therein. The outer tubular member of the connector assembly restricts the expansion of the inner tubular member as the male portion is inserted therein.

U.S. Pat. No. 4,846,193 to Tremulis et al., disclose a guidewire having first and second telescopically extendable sections movable between axially extended and retracted positions. No disengagement of the guidewire and extension wire is disclosed.

U.S. Pat. No. 4,966,136 to Kraus et al., discloses an internally threaded female connection member secured to the distal end of the extension wire. The internally threaded female connection member is disclosed to be freely rotatable with respect to the extension wire with securement thereto by means of a collar. The body of the extension wire has a distal enlargement which cooperates with the collar to permit it to be freely rotated. The female connection member of the extension wire cooperates with a threaded male portion located on the proximal end of the guidewire. The mechanism disclosed by Kraus et al., requires the difficult step of threading the segments into each other. Threading pieces having the diameters of a guidewire and an extension wire into each other can be difficult to accomplish, especially under operating room conditions.

U.S. Pat No. 4,827,941 to Taylor et al. discloses a guidewire-extension system employing a tubular female connector portion on one wire and a cooperating male portion on the other. The connecting male portion has an effective diameter in one radial dimension which is slightly larger than the inner diameter of the tubular portion. In a preferred practice, the male end portion of the Taylor et al. guidewire has an undulating shape, which, when inserted into the tube creates an interference friction fit.

U.S. Pat. No. 5,247,942 to Prather et al. discloses a guidewire with a swivel. The Prather et al. invention provides for permanent connection of a main part and an extension part. A swivel is included in the system to permit the permanently affixed parts to be rotated with respect to each other to enhance steerability of the main or guidewire segment. The Prather '942 structure has the same drawback as the Gambale '923 system discussed above.

U.S. Pat. No. 5,246,009 to Adams discloses a complicated guidewire assembly utilizing an inner core wire and an outer tube. Torque transmission is an aspect of the Adams invention.

U.S. Pat. No. 5,271,415 to Foerster et al. describes a guidewire extension system comprising a tubular outer body with guidewire and extension wire elements, e.g., helically wound wires, therein. The device of Foerster et al. has the same disadvantage as that of the Kraus et al. '136 patent, i.e., the interconnect step requires threading of the parts into each other. Moreover, the device described by Foerster et al., with brazed wires inside a tubular structure, may be difficult to manufacture.

The guidewire extension systems discussed above all have one or more drawbacks. Some are difficult or tedious or intricate to engage and disengage. Others do not disengage at all. While frictional engagement overcomes the disadvantages of crimping, disengagement may occur too easily. Problems of discontinuity at the guidewire/extension wire connection e.g., kinking, have been experienced with some systems. Moreover, prior extendable wires for use in coronary angioplasty procedures have been found to be unsuitable in peripheral arteries because the connections are not sufficiently strong. Further, some connections have larger diameters than the rest of the guidewire system. This may cause snagging of, e.g., over the wire catheters. It also means that the catheter with which such connection system is used must have a larger internal diameter lumen than would be necessary were a smaller diameter coupler employed.

Accordingly, a principal object of the present invention is to provide a guidewire extension system which is reliable, easy to use and easy to manufacture.

Another object of the present invention is to provide a guidewire extension system which does not require that either the guidewire or extension wire be rotated when attaching one to the other. It is advantageous that the guidewire be held stationary because the guidewire is located within the patient's blood vessel where unnecessary movement can induce trauma. It is also advantageous to have the majority of the length of the extension wire held stationary (e.g., by retention within a carrier structure) during the connection process. Having the extension wire self-contained in a tubular carrier package allows medical personnel to concentrate upon engaging the two wires using the present extension system. An uncontained extension wire is awkward, and thus complicates the process of effecting a guidewire/extension wire union during a medical procedure.

It is a further object of this invention to provide an easily attachable (and reattachable) and easily detachable guidewire extension system which has a readily identifiable tactile sensation, e.g., a "snap", when the system components are affirmatively attached.

It is still a further object of the present invention to provide a guidewire extension system which has substantially the same flexibility and pushability at its connection as that of the remainder of the length of the guidewire. The system provides an advantageously controllable coaxial alignment of the guidewire and extension wire.

It is yet another object of the present invention to provide a unitized guidewire extension system having a substantially uniform, smooth, continuous outer diameter or profile along the guidewire, connector, and extension wire. A smooth, continuous transition in external profile from the distal end of the guidewire to the proximal end of the extension wire, especially over the connector segment, permits an over-the-wire catheter to be positioned without becoming hung up. Methods of manufacturing an extension system of this invention and methods of using a system of this invention also are disclosed.

BRIEF SUMMARY OF THE INVENTION

Briefly, in one aspect, the present invention is an extension system for affirmatively connecting the proximal end of a guidewire to the distal end of an extension wire. In its connected form, the entire structure is sometimes referred to herein as an exchange wire. In one practice, a tactile "snap" is experienced by the user when guidewire/extension wire connection or docking is achieved.

In accordance with one aspect of the present invention, there is provided a coupler for a guidewire/extension wire system, the coupler comprising a male segment and a cooperating female segment. The coupler of this invention permits multiple coupling and decoupling, as needed, of the guidewire/extension wire to which it is attached. The male and female segments are fixedly attached to one or the other of the distal end of the extension wire or the proximal end of the guidewire, and yet the system permits either or both of the guidewire/extension wires to be freely rotated with respect to each other without the structural complication of a separate swivel.

The female coupler segment of this invention comprises a hollow, elongate sleeve, the sleeve having opposite ends and a sleeve wall which defines inside and outside sleeve diameters, one of said ends having an inside diameter such that it can be firmly attached to one of said guidewire or said extension wire, the other of said ends defining a lip, and a plurality of lateral slots, said slots intersecting said lip so that the lip can be separated by insertion of said male segment. In a preferred practice, the lip is circular or semi-circular and is defined by one end of the sleeve.

The male coupler segment of this invention comprises an elongate member located on the other of the guidewire or extension wire. The elongate member has an exterior surface and opposite ends which are referred to herein, as insertion or leading and following or connection ends, respectively. The insertion or leading end of the elongate member is the first portion of the elongate member to enter the female sleeve in the coupling process. The male coupler segment is affixed to the proximal end of the guidewire or the distal end of the extension wire, as appropriate. Several attachment locations and methods of attachment are discussed below. The exterior surface of the elongate member defines at least a portion of a radial groove and an annular shoulder in the following end, the groove having a diameter which cooperates with the female coupler segment lip so that when said male member is inserted into said female segment, the lip passes or slides along the exterior surface of the member in a slightly separated position, passes over said shoulder and returns to a non-separated position within the groove or notch. In this manner, the female coupler segment is retained substantially coaxially along the male coupler segment after insertion. Coupling occurs with a tactile sensation that insertion is completed, e.g., with an identifiable "snap".

The extent of coaxial alignment can be controlled by adjusting the length of the overlap between the male coupler segment and the female coupler segment. For example, if a relatively longer male coupler segment is used, i.e., an elongate member which is relatively longer between its leading end and its groove, then axial alignment of the connected ends of the guidewire/extension wire is more rigidly maintained. Conversely, if a shorter male member (up to and including a substantially spherical ball) and a corresponding sized female coupler segment are used, then the axial rigidity of the overlapped coupler segments will be relatively minimal.

One of the advantages of this invention is that the male member and the female coupler are conveniently coupled and decoupled using insertion and withdrawal forces easily applied by medical personnel. They are not permanently affixed to each other and no restriction or frictional fit is created. Neither of the male nor the female coupler segments are threaded, thereby eliminating the need to create those threads. This also eliminates any need to thread relatively small components into each other during a coupling/decoupling sequence. In practicing this invention, no rotation of either part is required in order to achieve coupling and decoupling.

One skilled in this art will appreciate that there are likely to be a number of structural equivalents to the "lip" and "groove" construction described above. All of such constructions are within the scope of the present invention. For example, instead of a lip on the female coupler segment, one or more dimples or protrusions (or a series or locus of dimples or protrusions) could be machined, stamped, or molded therein. In that embodiment, the male segment would have surfaces, detents, or dents which would cooperate with the dimples to provide a tactile sensation at coupling and to couple the segments. A slide-stop (such as that mentioned in U.S. Pat. No. 5,247,942) could be used if the cooperating surfaces of the slide and stop permitted the slide/stop to be decoupled using decoupling or withdrawal forces in the range discussed below.

It will also be appreciated that a "lip", as that term is used herein, may be located within the coupler sleeve rather than at one end. In such an arrangement, an intermediate narrow region or lesser diameter segment would be stretched, expanded or moved further within the coupler sleeve to create the tactile sensation of connection as the male member passed therewithin. Lateral slots could be utilized and could pass through the intermediate narrow region to permit the male member to pass therethrough more easily.

In a preferred practice of this invention, the female coupler sleeve has two lateral slots, the slots being generally oppositely disposed.

In a further practice, the outside diameter of the male coupler segment, as defined by its exterior surface, is less than the inside diameter of the female coupler sleeve, leaving an annular space therebetween and precluding a possible restriction or frictional interaction between the cooperating segments.

In yet a further preferred practice, the male member has a tapered insertion end, permitting easy insertion of said male member into the female coupler sleeve.

A guidewire extension system of this invention can be used to connect an otherwise conventional extension wire to a steerable guidewire having a plurality of multifilar, oppositely wound coils. Of course the guidewire also may have only a single coil, depending upon application. For smaller diameter guidewire applications, e.g., 0.014 in. diameter coronary wires, a guidewire core having no coil at all may be used.

In another practice, the female segment is disposed on the distal end of the extension wire and the male segment is disposed on the proximal end of the guidewire.

BRIEF DESCRIPTION OF THE FIGURES

The present invention may be better understood with reference to the detailed description below and the attached FIGURES wherein like reference numerals designate like features throughout, and wherein:

FIG. 3A is an end view of the segment shown in FIG. 3;

DETAILED DESCRIPTION OF THE INVENTION

Figure 1:
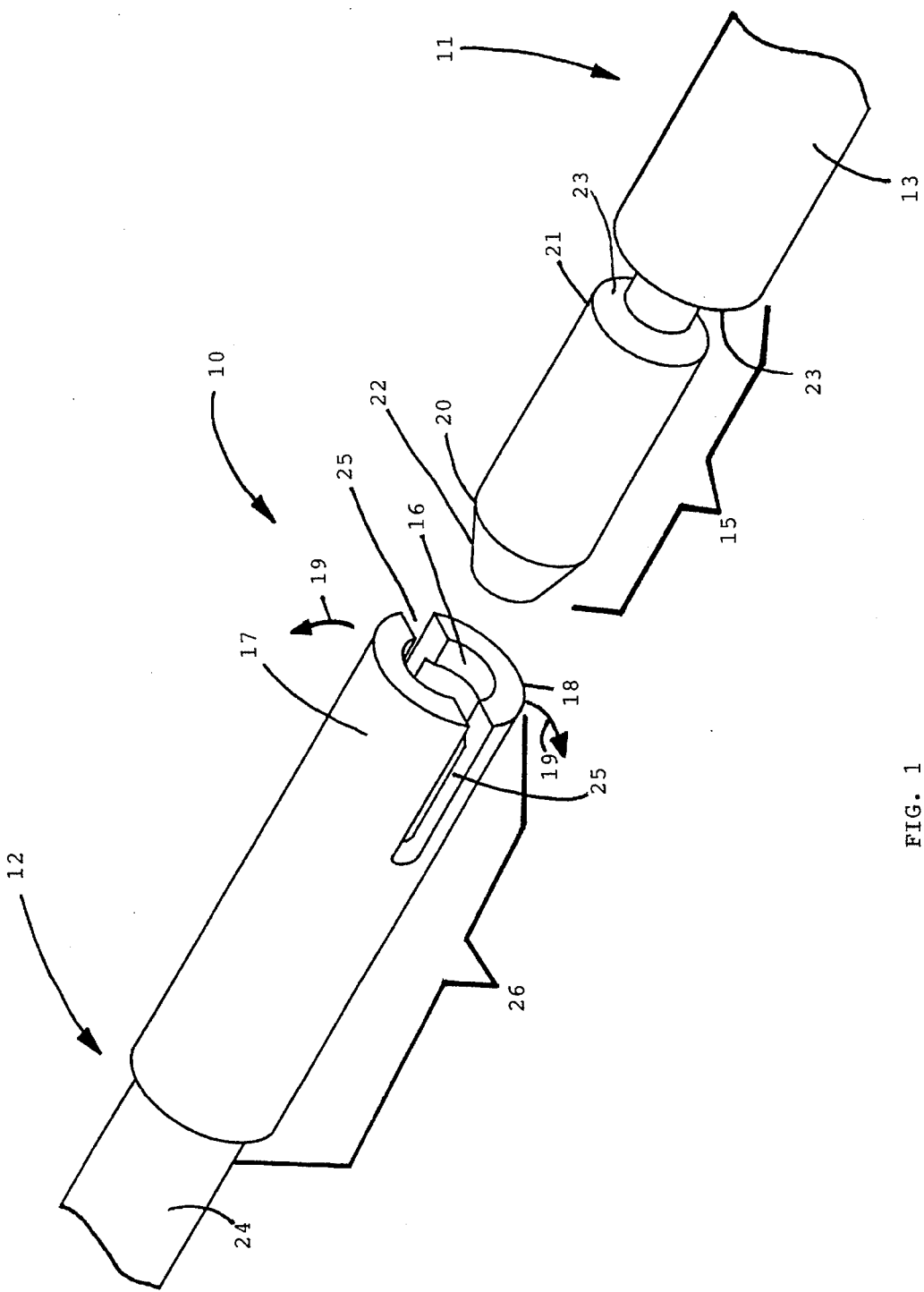
FIG. 1 is a perspective view of an embodiment of the present invention.

As is shown in FIG. 1, a guidewire extension system 10 embodying features of the present invention has a guidewire or main section 11 which is adapted to be inserted into a patient's vascular system and an extension wire or extension section 12 which can be connected and disconnected to the main section 11. Connection and disconnection of guidewire 11 and extension wire 12 facilitates catheter exchange without the need for removing the main guidewire section 11 from the patient's vascular system. In the embodiment shown, guidewire section 11 generally comprises an elongated shaft 13 having a distal end (not shown in FIG. 1) with a male coupler segment 15 located at its proximal end. (The details of a preferred guidewire structure are discussed below.) Shaft 13 optionally may be covered with a polymeric, e.g., polytetrafluoroethylene (PTFE), polyurethane, or other coating (not shown). Single filar coils, multifilar coils, radiopacity markers, or other commonly utilized guidewire structures, may be disposed on shaft 13. These structures have been omitted from this description of the invention for purposes of clarity.

Extension section 12 has an elongated shaft 24 with a hollow female coupler segment 26 secured to its distal end. Female coupler segment 26 may be fixed to extension wire 24 using techniques well known in this art such as resistance welding, crimping, gluing, soldering, or brazing. Female coupler segment 26 may comprise, for example, a suitably modified section of hypotube brazed to the distal end of an extension wire. Female coupler segment 26 may also be machined from a segment of solid, cylindrical core workpiece. Powder metallurgy techniques also may be used to manufacture female coupler segment 26.

Also shown in FIG. 1 are the plurality of longitudinal slots 25 and a circular lip 16. Slots 25 intersect and divide circular lip 16 producing opposite, semicircular tabs 17, 18 which can be radially separated (in the direction of arrows 19) as male and female segments 15 and 26 are mated. Slots 25 may be machined into coupler segment 26 using conventional grinding and cutting operations or they may be created by any of a number of other known processing techniques including electrical discharge machining. The portion of the shaft 24 proximal to the female member 26 may be covered with, e.g., a polymeric, or other type of coating.

Male connector segment 15 is elongate, having opposite leading or insertion and following ends 20, 21 respectively. In this embodiment, insertion end 20 is tapered (at 22) to ease the connection process. The exterior surface of male connector segment 15 further defines a radial groove 23.

Figure 2:
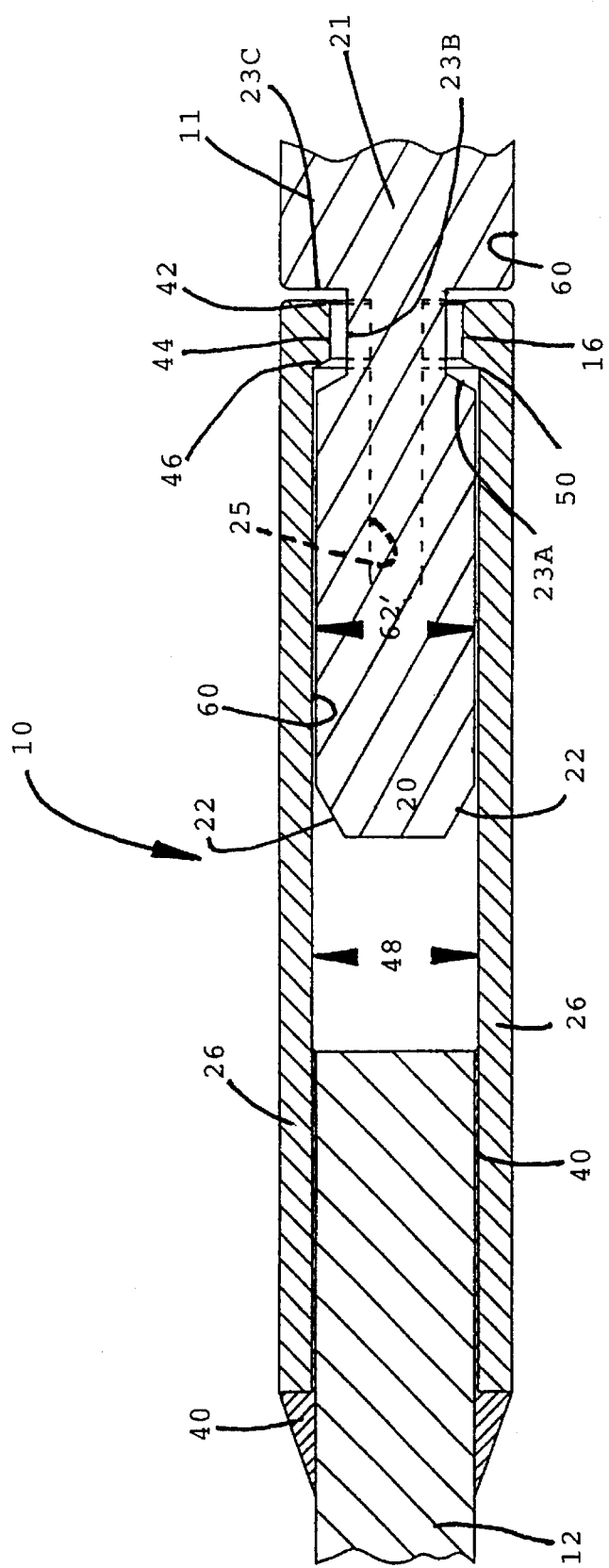
FIG. 2 is a cross-sectional view of the embodiment of the invention of FIG. 1 after the connector segments have been mated.

FIG. 2 illustrates the detailed interaction between lip 16 and radial groove 23. FIG. 2 is a cross-sectional view of an embodiment of the invention 10, shown in FIG. 1, after the segments have been coupled or "snapped" together. In this embodiment, female coupler segment 26 comprises a section of hypotube which has been brazed (at 40) to extension section wire 12. Other methods of securement, e.g., soldering, or gluing, may be employed. As is shown, the glue, solder, or braze zone itself can be employed to provide a smooth transition between the guidewire or extension wire to which the female coupler segment is attached and to the coupler segment itself.

A circular lip 16 of this invention is described in greater detail as follows. Circular lip 16 has a slightly rounded or tapered leading or opening edge 42, a substantially uniform or single diameter intermediate portion 44 and an angled or rounded interior edge or shoulder 46 which merges (at 50) to the interior diameter 48 of the hypotube section 26. Angled interior edge 46 can be, for example, the byproduct of drilling to create interior diameter 48. Interior edge 46, in cooperation with the configuration of radial groove 23, determines at least the magnitude of the force needed to disengage male and female coupler segments 15 and 26. Other factors such as the material employed, its treatment prior to incorporation into the present coupler, and the precise interaction between the slots and tabs also affect the magnitude of withdrawal forces.

The details of male coupler segment 15 also are shown in FIG. 2. Male coupler segment 15 (best seen in FIG. 1) is defined by the configuration of exterior surface 60 of the male segment of the connector system. As was discussed above, male segment 15 has an insertion end 20 and a following end 21. Insertion end 20, in this embodiment, is rounded or tapered (at 22) to provide ease of insertion. The outside diameter 62 of the male segment 15 leads to and defines radial groove 23. Radial groove 23, in this embodiment, comprises an angled, radiussed, or perpendicular annular shoulder 23A, a neck 23B which has a uniform diameter, and a radial stop surface 23C. Radial stop surface 23C can be disposed substantially perpendicularly to the axis of the guidewire extension wire system, as is illustrated, or it may be filleted or shaped to provide a more rounded stop. As shown, interior edge 46 of female coupler segment 26 is angled so as to be complimentary with and to cooperate with annular shoulder 23A when lip 16 is lying within radial groove 23. Radial stop surface 23C normally controls the extent to which the male and female coupler segments can be engaged, provided the elongate member is short enough to fit completely within female coupler segment 26 and not abut against the extension wire main section. For purposes of orientation, longitudinal slot 25 is shown in phantom.

Three significant observations should be made with respect to the embodiment of FIG. 2. First, the interior diameter 48 of female coupler segment 26 is larger than the outside diameter 62 of male coupler 15. This fact means that no restriction or frictional fit is needed for coupling to occur between the male and female segments. The absence of a restriction fit also permits male and female coupler segments 15, 26 (and therefore the guidewire or extension wire to which they are attached) to rotate freely with respect to each other. In other words, this embodiment of the invention obviates the need for a structure like the swivel of U.S. Pat. No. 5,117,838 (Palmer et al.) described above.

The second important observation is that the structure shown in FIG. 2 provides a definite tactile "snap" when the segments are coupled. A sound may also be heard, especially in the larger sized peripheral wires. Whether a sound is generated or not, the tactile sensation of coupler engagement is a significant indicator to the system user that coupling is complete. A small amount of play, as shown in the system illustrated, also permits the physician to move the coupler segments with respect to each other and thereby establish that proper engagement has occurred.

Thirdly, this system permits multiple, affirmative engagement and disengagements of the male and female segments, i.e., multiple catheter exchanges, can be accomplished. This is yet a further advantage over the prior art coupler systems which require permanent connection of the segments.

Figure 3:
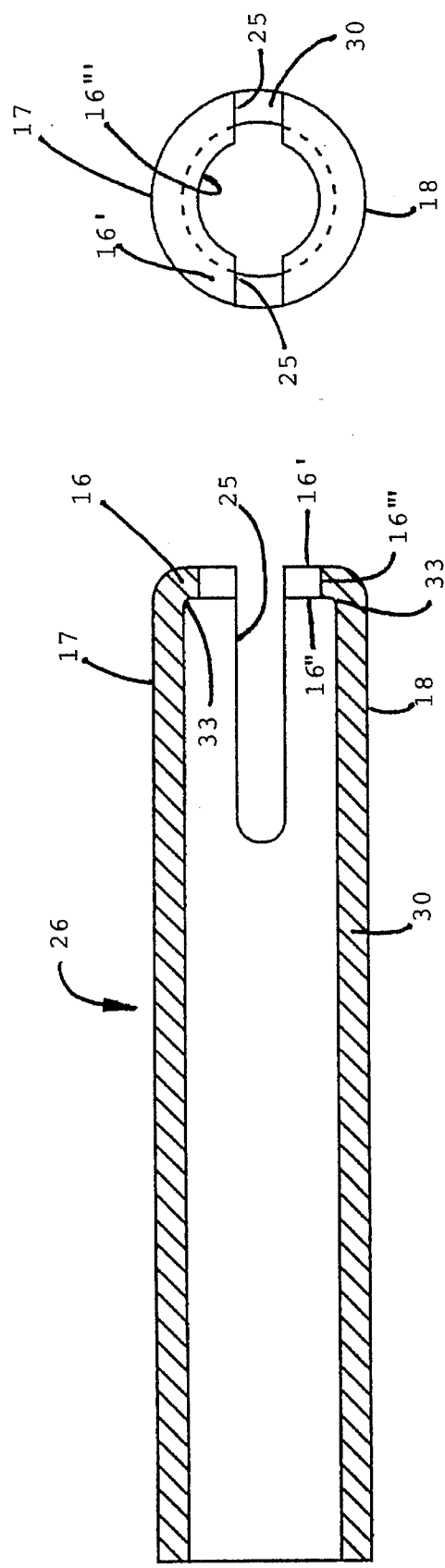
FIG. 3 is a sectional view of a female connector segment of this invention.

FIG. 3 is a sectional view of a portion of the female coupler segment 26 of the present invention. FIG. 3A is an end view of the female coupler segment shown in FIG. 3. In particular, female coupler segment 26 comprises a hollow tubular body 30 having a substantially circular lip 16 with longitudinal slots 25 therein. Lip 16 has outside and inside edges 16', 16", respectively, with a radial surface 16''' therebetween. Lip 16 can be formed by any of several techniques. However, in the embodiment shown, lip 16 was formed by coining a segment of hypotube. This technique of formation is to be contrasted with that of FIG. 2 where drilling, cutting, and grinding steps were employed. It is noted that coining lip 16 tends to create a more rounded or radiussed intersection (at 33) between tubular body 30 and lip 16 than the same intersection (at 50) in FIG. 2. The configuration of the interior intersection between the lip 16 and tubular body 30 will, to some extent, determine connector withdrawal forces.

Slots 25 and lip or tabs 16 define flaps 17 and 18 which move from a substantially parallel, axial, alignment to a slightly oblique alignment (with respect to the system axis) in the coupling process. In the connection step, radial surface 16''' slides along the exterior surface 60 of the male segment, separating the semicircular flaps 17, 18 to a slightly opened position. Tubular body 30 biases flaps 17, 18 toward each other and tends to reduce the radial width of slot 25. When the connection is made, flaps 17, 18 return to substantially their original position, a "snap" is heard or felt (or both), and the coupling process is completed. When the coupling process is complete, interior edge 16" aligns in substantially parallel fashion with shoulder 23A on male connector segment 15.

Figure 4:
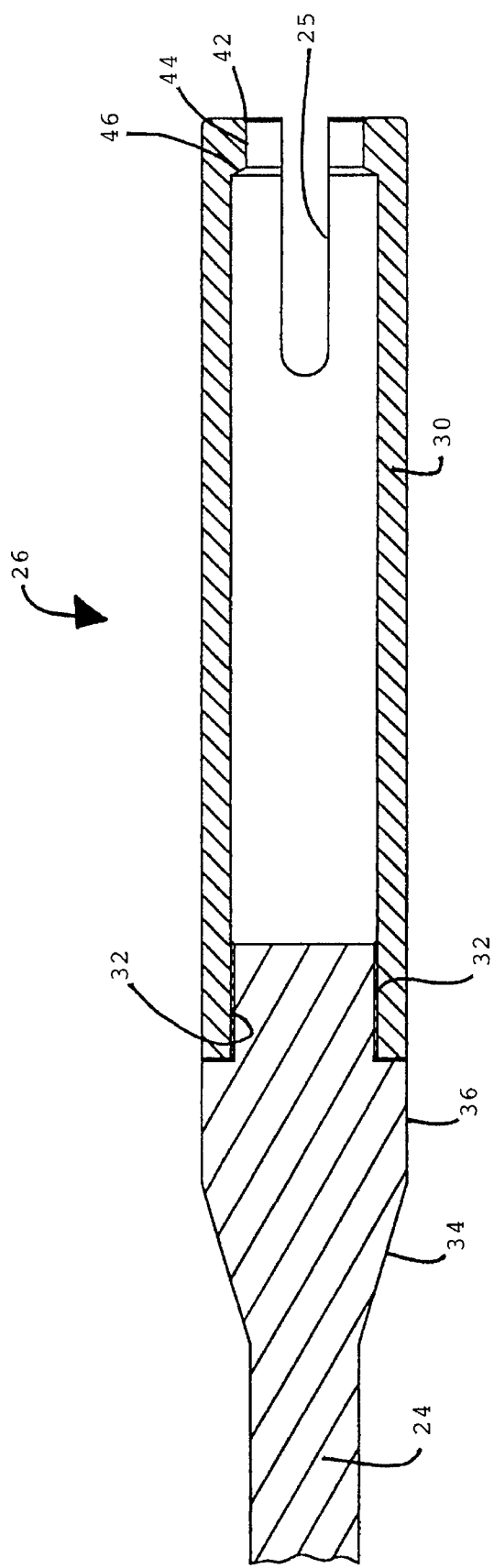
FIG. 4 is a sectional view showing the structure of an attachment between a female coupler segment of this invention and the extension wire to which it is attached.

FIG. 4 shows in section the details of one possible approach to attaching female coupler segment 26 to elongated shaft 24. As was discussed above, in a preferred embodiment, elongated shaft 24 is the distal end of an extension wire but may also be the proximal end of a guidewire or main wire. Hollow tubular body 30 is attached to shaft 24 at resistance weld or spot weld 32. As is noted above, other techniques for attachment may be used. In FIG. 4 the elongated shaft segment coupled to tubular body 30 is shown to be ramped or tapered at 34. Taper 34 leads to an extension wire segment 36 which has substantially the same outside diameter as that of hollow tubular body 30. Elongated shaft 24 has been ground to a smaller diameter than wire segment 36 to enhance flexibility. Taper 34 therefore provides a gentle transition between the extension wire body and tubular body 30 which is particularly desirable. Taper 34 permits a catheter to pass over hollow tubular body 30 (e.g., during a catheter exchange process) without becoming caught on the connector system structure.

Figure 5:
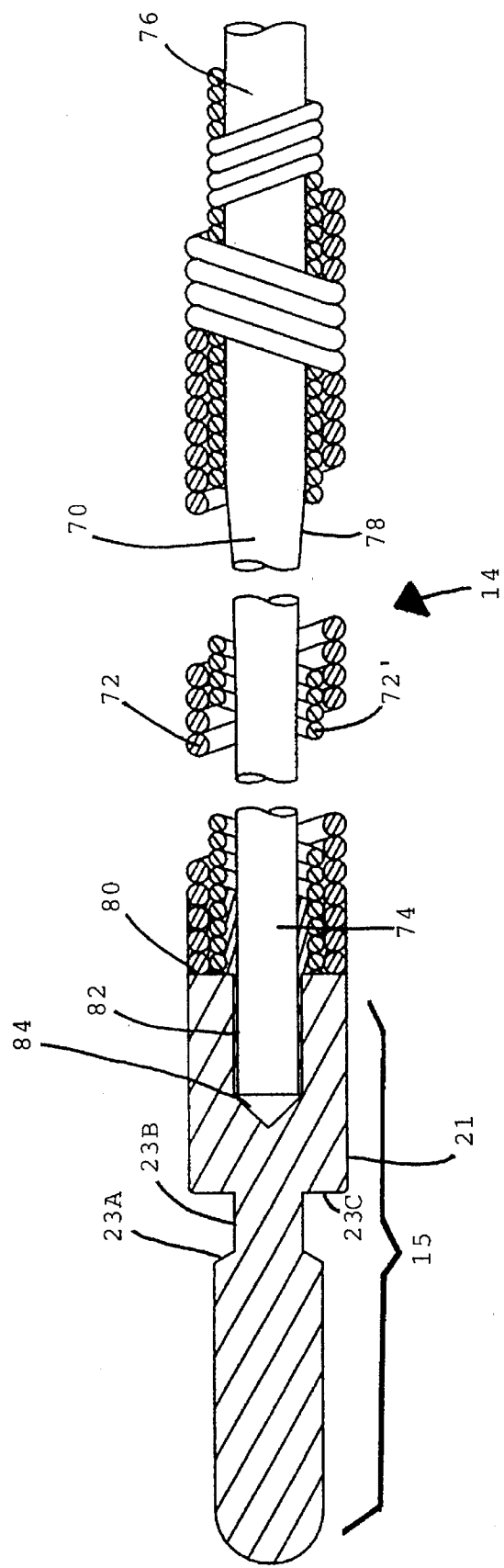
FIG. 5 is a partial sectional view of a male coupler segment of this invention.

FIG. 5 illustrates one possible connection structure between a guidewire proximal end 14 and a male coupler segment 15. The particular guidewire structure employed is that of a core wire 70 having oppositely wound multifilar coils 72, 72' disposed therearound. Core wire 70 has a reduced diameter proximal segment 74 which connects to core wire main section 76 through taper 78. Coils 72,72' and reduced diameter proximal segment 74 are attached to male coupler segment 15 e.g., by brazing, at 80 and 82, respectively. Male coupler segment 15 is brazed to guidewire proximal end 82 at bore 84 which is drilled or machined in the following end 21 of male coupler segment 15. It is important that there be a smooth transition from male coupler segment 15 to the remaining structure of the guidewire so that a catheter can slide smoothly thereover during an exchange process.

Figure 6:
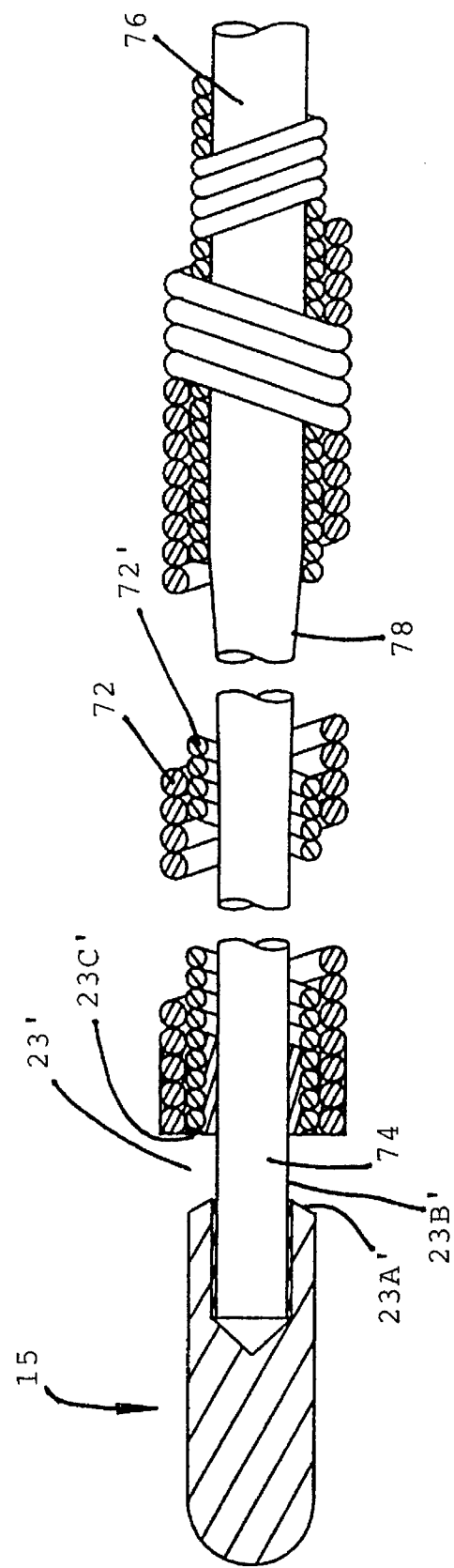
FIGS. 6, 7, 8, 9 and 11 are partial sectional views of further embodiments of male coupler segments of this invention.

FIG. 6 illustrates another embodiment of the invention wherein groove 23' comprises a shoulder 23A', a portion of reduced diameter segment 74 indicated at 23B' and the proximal end of coils 72, 72' indicated at 23C'. There are many possible ways to construct a groove which will cooperate with a connecting female segment in accordance with this invention.

Figure 7:
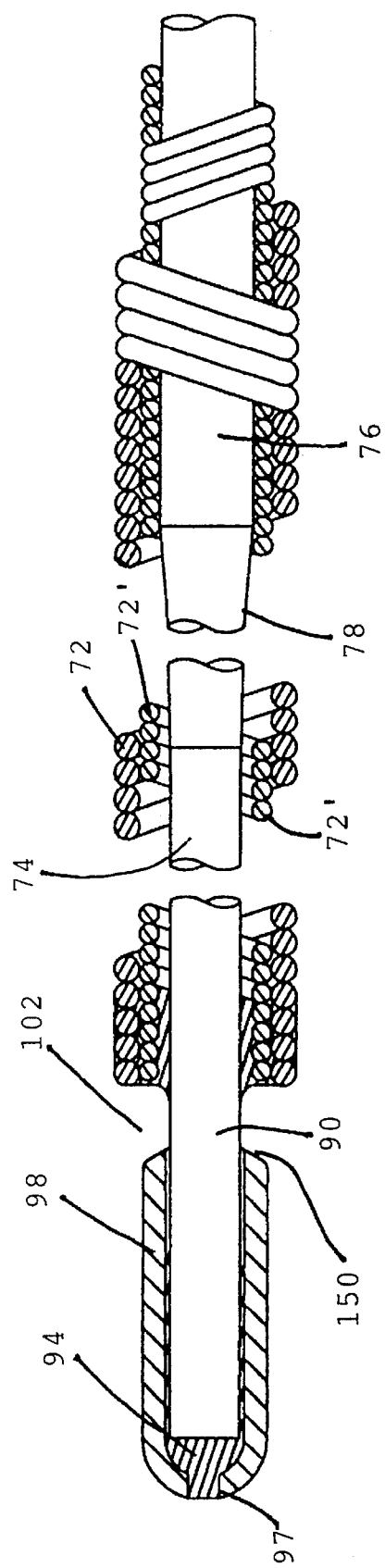
Figure 8:
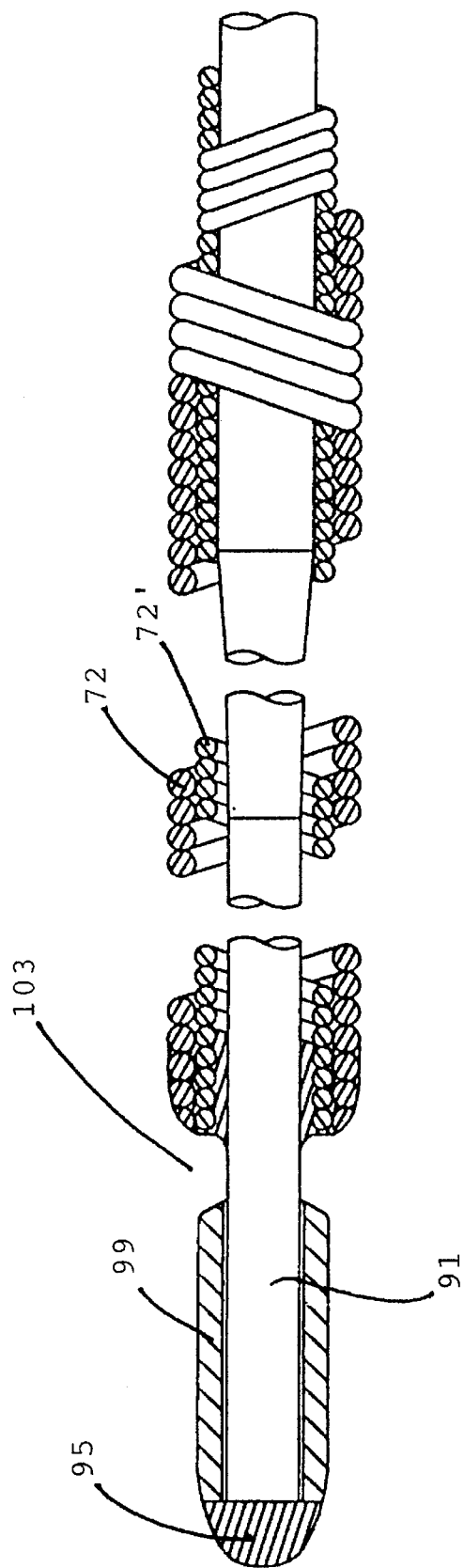

FIGS. 7, 8, 9, and 11 illustrate variations in construction of a male connecting segment of this invention. The variations illustrated are alternative ways in which the desired external configuration of the male coupler segment can be created. In each of the systems illustrated, a reduced diameter proximal guidewire segment 90, 91, 92, 93, respectively, is attached (at 94, 95, 96, and 97, respectively), to elongate male connector segment 98, 99, 100, and 101 respectively. In each instance a groove 102, 103, 104, and 105 is created or defined. FIG. 7 illustrates a coined sleeve that is attached to the wire core 90 by application of glue, solder, or braze through opening 97 on the insertion end of the segment 98. This procedure keeps annular shoulder 150 clean. FIG. 8 illustrates a plasma ball weld 95 utilized on the insertion end of male connector segment 99.

Figure 8A:
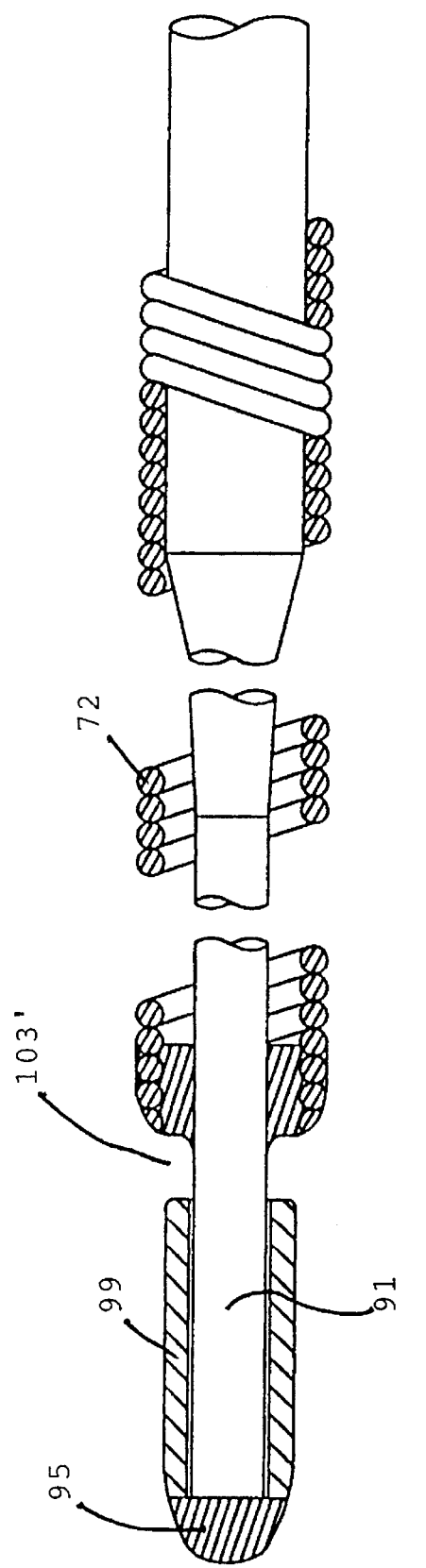

FIGS. 8, 8A and 8B illustrate different sized guidewires in which the present invention has been used. For example, the guidewire shown in FIG. 8 would be the structure of a 0.035 in. and 0.038 in. diameter guidewire having two counterwound spring coils 72, 72'. The embodiment of FIG. 8A has a single spring coil 72 and would be structure employed in a 0.025 in. diameter guidewire.

FIG. 8B is a structure useable for very small diameter, e.g., 0.014 in., guidewires. No spring coils are used. The extreme proximal end of the guidewire is ground to a lesser diameter and groove 103" is defined by elongate male connector segment 99, a reduced diameter segment 152, and taper 154.

Figure 9:
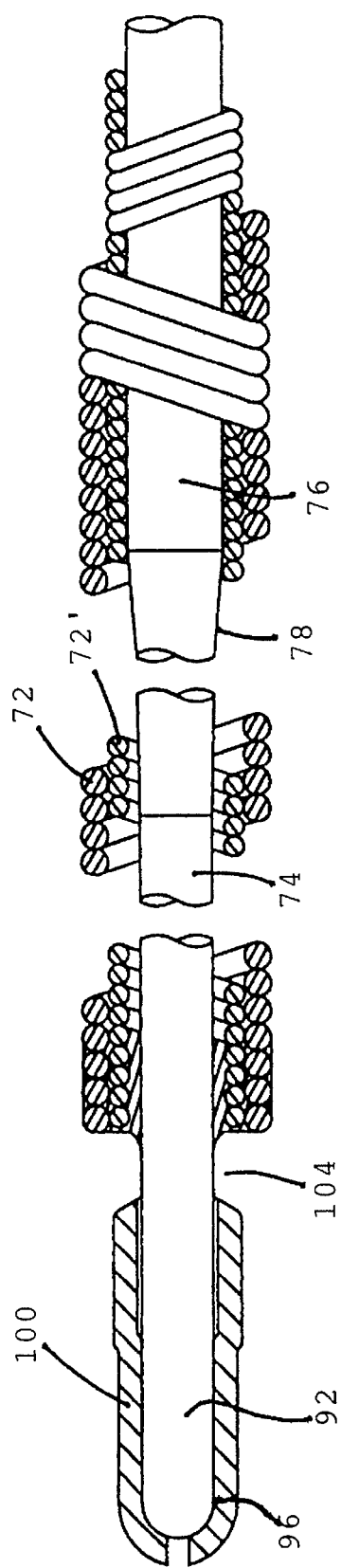

FIG. 9 shows a sleeve which was crimped (at 96) on the guidewire body core 92.

Figure 11:
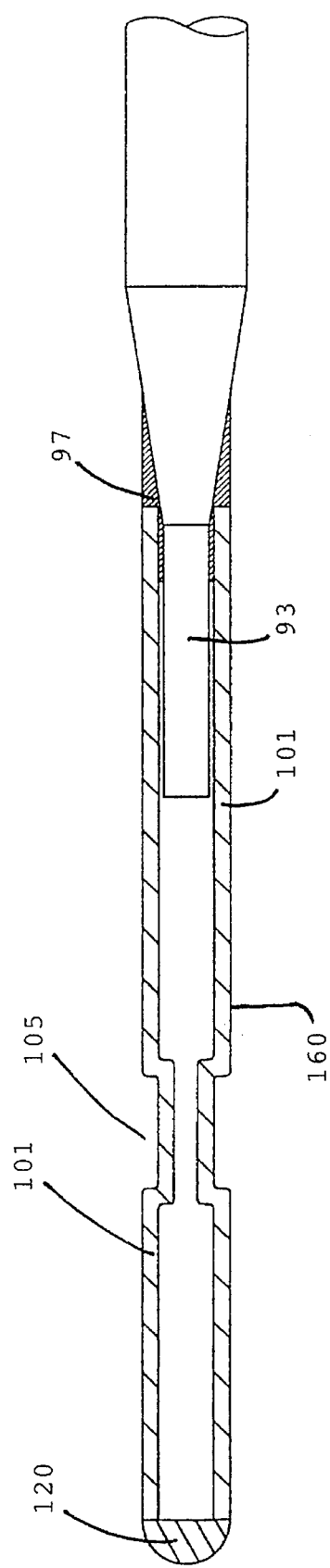

FIG. 11 illustrates an embodiment where the requisite external configuration of the male segment is externally formed into a segment of hypotube 160. Hypotube 160 then is brazed onto the proximal end of the guidewire and a rounded tip 120 is created on the remaining end.

Figure 10:
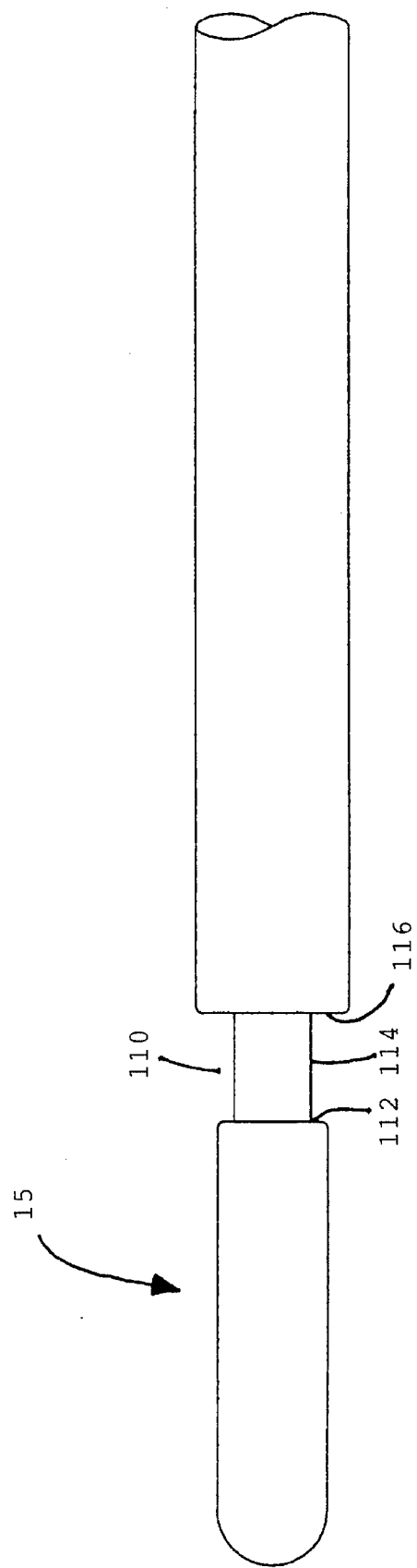
FIG. 10 is a side view of a male coupler segment of this invention.

FIG. 10 illustrates an embodiment of the invention wherein the male connector segment external configuration 15 is simply machined into the proximal section of the guidewire, e.g., by centerless grinding. A radial groove or notch 110 defined by surfaces 112, 114, and 116 cooperates with the lip portion of the female coupler segment.

Figure 12:
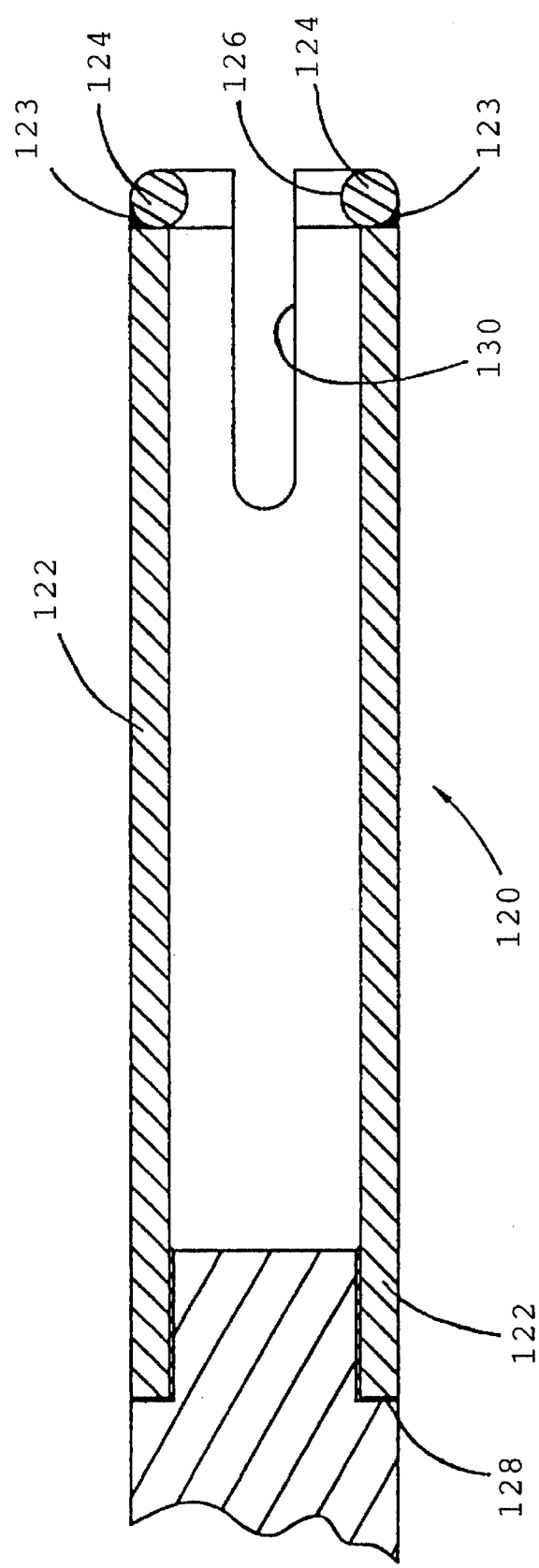
FIG. 12 is a sectional view of an alternative female coupler sleeve of the present invention.

FIG. 12 is a sectional view of an alternative embodiment of a female coupler segment 120 of this invention. In FIG. 12 a section of hypotube 122 has a metal ring 124 brazed, soldered or glued (at 123) to its open end. Metal ring 124 has a diameter which is slightly less than the inside diameter of the hypotube 122 and thereby creates a lesser diameter lip 126. As shown, this approach produces a substantially circular lip. Hypotube section 122 then is resistance welded, glued, soldered or brazed to the guidewire or extension wire core (at 128) with which it is associated. Electrical discharge machining or other known fabrication techniques then are used to create lateral slot 130. Alternatively, ring 124 could be fitted inside of hypotube segment 122 to create an inwardly disposed "lip" as is discussed above. Regardless of the location of the lip, as long as the female and male segments overlap sufficiently, kinking at the connection will be reduced.

The main guidewire section 11 is intended for use in positioning a catheter (not shown) in the vasculature of a patient, and it has a length corresponding to the length of a conventional guidewire for this purpose. Details of typical catheters and guidewires can be found in U.S. Pat. No. 4,538,622 (Samson et al.) and U.S. Pat. No. 4,569,347 (Frisbie). Those patents are incorporated by reference herein in their entirety.

Extension wire 12 is sufficiently long so that when the main guidewire section 11 and extension wire 12 are connected together, the guidewire system or exchange wire 10 has an overall length suitable for catheter exchange without removing the main guidewire 11 from the patient's vascular system. With a catheter having a length on the order of about 65 cm to 175 cm, for example, guidewire 11 would have a length of about 100 to about 200 cm, and extension wire 12 would have a length of about 100 to about 200 cm (or longer).

Shafts 13 and 24 and female segment 26 can be fabricated from essentially any suitable material, such as stainless steel, Elgiloy, or the shape memory alloy referred to as Nitinol (55% Ni-Bal. Ti). Each should have an overall largest diameter which allows, e.g., a dilatation catheter, to pass freely thereover. Preferably, the two shafts 13 and 24 are provided with a smooth transition between them. Either or both of shafts 13, 24 can be provided with a coating of polymers or elastomers such as PEBAX polyamide, polyurethane, polytetrafluoroethylene (PTFE), or other such material well known to one skilled in this art.

Typical dimensions of the main guidewire section include an outside diameter of the shaft 13 of about 0.009 to about 0.065 inch, an outside diameter of the male insertion segment about 0.006 inch to about 0.050 inch and a length of about 0.025 to about 0.250 inch. The female connector segment has dimensions which generally cooperate with the male segment dimensions and a length of about 0.060 inches to about 0.500 inches and an outside diameter of about 0.009 in. to about 0.065 in. While this invention is particularly applicable to the larger diameter guidewire, e.g., 0.038 inches and 0.035 inches, smaller diameter applications, e.g., 0.025 inches or less, down to 0.009 inch diameter wires, are also within its scope. Generally speaking, the ratio of male segment outside diameter to length and female segment inside diameter to length will fall in the range of 1:10 to about 1:1, but more likely will fall in the range of 1:5 to about 3:5. Having a length which is larger than the respective diameter tends to keep the wires more axially aligned, thereby minimizing unwanted bending and kinking.

Percutaneous transluminal angioplasty is a medical procedure in which the present invention can be used. In use, the main guidewire section 11 is percutaneously introduced into the vascular system of a patient with a dilatation catheter through the skin by means of an introducer (not shown). The distal tip of the guidewire is advanced beyond the distal tip of the dilatation catheter while the latter is held in place. The main guidewire section 11 is advanced into the selected vessel. The guidewire tip is preferably advanced through the lesion and beyond it, in order to permit the balloon portion of the dilatation catheter to be positioned within the lesion over a more supportive section of the guidewire. Once in position, the main guidewire section 11 is held in place and the dilatation catheter is advanced along it until the inflatable balloon thereof is within the lesion. Male connector segment 15 remains outside the patient's body and outside any adapter which may be connected to the proximal end of the dilatation catheter. If necessary, e.g., to retain a sufficient length of the main guidewire section 11 outside the catheter for the physician to grip, the guidewire and catheter may be advanced together substantially in unison.

To exchange catheters, the main guidewire section 11 is extended by manually snapping the female tubular member 26 onto the male member 15. When the two guidewire sections are engaged, the dilatation catheter can then be withdrawn from the patient's body over the extended guidewire system.

A new dilatation catheter may then be introduced over the extension section 12 and advanced along the main guidewire section 11 within the patient's body until the balloon crosses the lesion. Once the proximal end of the new catheter has advanced beyond the connection between female member 26 and male member 15, section 12 can be removed from section 11 by unsnapping the female member 26 by pulling the two sections apart. This can be accomplished without disturbing the position of the main section 11 in the patient's body.

The above description describes utilization of the present invention primarily in coronary angioplasty catheter exchange. It is to be understood that this invention has application in essentially any procedure where a catheter is utilized for diagnostic or interventional applications.

This invention has a number of important features and advantages. The two sections of the guidewire can be connected together whenever a longer, exchange wire is needed, and they can be disconnected whenever the additional length is not required. The two sections of the guidewire may be connected and disconnected (and reconnected, if desired) by the physician by simply "snapping" and "unsnapping" the male segment into or out of the female segment. Subsequent to engagement, the segments can be freely rotated with respect to each other (e.g., to permit the guidewire to be steered) and can easily be disengaged. This can be done as needed, and no special tools are required whether to make the connection or to separate it. Thus, catheter exchange is greatly simplified. This also permits the same guidewire to be repositioned to second and multiple additional vascular sites which then may be treated with different catheters, making the present system very versatile.

As noted in the previous paragraph, a guidewire extension system of this invention can be multiply engaged and disengaged. The present invention therefore permits two or more catheter exchanges, during a medical procedure, without a need to reposition or exchange the main or guidewire. Generally speaking, the ease of disengagement (i.e., the pounds of force needed to disengage an extension wire from a guide wire) has been found to be in the range of about 0.2 to about 5.0 lbs., preferably about 0.3 to about 3.0 lbs., and most preferably about 0.7 lbs. to about 2.0 lbs. Factors which affect withdrawal forces include the overall device diameter (withdrawal forces being higher for larger diameter devices), wall thickness of the tube, slot configurations, the materials of which the male and female coupler segments are made, and the relationship between the cooperating surfaces on the male and female coupler segments. The more abrupt or acute the relationship, the higher the withdrawal forces. With reference to FIG. 2, the more nearly perpendicularly (relative to the axis of the device) shoulder 23A engages surface 46, the more difficult withdrawal of male coupler segment from the female coupler segment.

It is apparent from the foregoing that a new and improved extended guidewire system has been provided. While the present invention has been described herein with the male connecting element fixed to the distal end of the main guidewire, and the female member located on the distal end of the extension section, it is obvious that the female connector member and male connector member may be interchanged. Moreover, it will be apparent to those familiar with the art that other modifications and improvements can be made without departing from the scope of the invention as defined by the following claims.

What is claimed is as follows:

1. A coupler for a guidewire/extension wire system, the coupler comprising:

a male segment and a cooperating female segment, the male and female segments each being attached to one or the other of the distal end of the extension wire or the proximal end of the guidewire, the female coupler segment comprising:

a hollow, elongate sleeve, the sleeve having opposite ends and a sleeve wall which defines inside and outside sleeve diameters, one of said ends having an inside diameter such that it can be attached to one of said guidewire or said extension wire, the other of said ends defining a lip, and a plurality of slots, said slots intersecting said lip so that the lip can be separated by insertion of said male segment, the male coupler segment comprising:

an elongate member, the member having an exterior surface which defines an outside diameter which is less than said sleeve inside diameter, and oppositely disposed insertion and following ends, the exterior surface of said member defining a radial groove and an annular shoulder on said following end, said groove having a diameter which cooperates with said lip so that when said male segment is inserted into said female segment to couple, rotatively the female segment to the male segment, said female coupler segment is retained along said male coupler segment with an annular space therebetween, and coupling occurs with a tactile indication that insertion is complete and without the creation of a frictional fit between the segments, whereby said male segment and said female coupler segments are conveniently coupled and decoupled.

2. A coupler according to claim 1 wherein the female coupler sleeve has two lateral slots.

3. A coupler according to claim 1 wherein the outside diameter of the elongate member, as defined by its exterior surface, is less than the inside diameter of the female coupler, leaving an annular space therebetween.

4. A coupler according to claim 1 wherein the tactile indication of a "snap" is experienced when the female segment and male member are completely intercoupled.

5. A coupler according to claim 1 wherein the male member has a tapered insertion end, the taper permitting easy insertion of said male member into said female coupler.

6. A coupler according to claim 1 wherein the female segment is disposed on the distal end of the extension wire and the male member is disposed on the proximal end of the guidewire.

7. A coupler according to claim 1 wherein the guidewire comprises a steerable guidewire having a core wire and a helical coil disposed about its distal end.

8. A coupler for a guidewire/extension wire system, the coupler comprising:

A male segment disposed on the proximal end of the guidewire, and a cooperating female segment disposed on the distal end of the extension wire, the female segment comprising:

a hollow, elongate sleeve, the sleeve having opposite ends and a sleeve wall which defines inside and outside sleeve diameters, one of said ends having an inside diameter such that it can be firmly attached to said extension wire, the other of said ends defining a circular lip, and a plurality of lateral slots, said slots intersecting said lip so that the lip can be separated by insertion of said male segment, the male coupler segment comprising:

an elongate member, the member having an exterior surface which defines an outside diameter which is less than said sleeve inside diameter, and opposite leading and following ends, the exterior surface of said member defining a radial groove and an annular shoulder on said following end, said radial groove having a diameter which cooperates with said lip so that after said male segment is inserted into said female segment, said male segment is retained within said female segment with an annular space therebetween, is rotatively coupled thereto, and coupling occurs with a tactile indication that insertion is complete as said lips return to a substantially non-separated position and without the creation of a frictional fit between the segments.

9. A coupler according to claim 8 wherein the female coupler sleeve has two lateral slots.

10. A coupler according to claim 8 wherein the outside diameter of the male member as defined by the exterior surface is less than the inside diameter of the female coupler, leaving an annular space therebetween.

11. A coupler according to claim 8 wherein the tactile sensation of a "snap" is experienced when the female segment and male member are completely intercoupled.

12. A coupler according to claim 8 wherein the male member has a tapered leading end, the taper permitting easy insertion of said male member into said female coupler.

13. A coupler according to claim 8 wherein the guidewire comprises a steerable guidewire having a plurality of multifilar, oppositely wound coils disposed about its distal end.

* * * * *